(12) United States Patent
Gupta et al.

(10) Patent No.: US 12,121,344 B2
(45) Date of Patent: *Oct. 22, 2024

(54) SYSTEMS AND METHODS FOR ANATOMICAL ALIGNMENT

(71) Applicant: Medos International Sarl, Le Locle (CH)

(72) Inventors: Saurav V. Gupta, Medway, MA (US); Mark Hall, Bridgewater, MA (US); Roman Lomeli, Plymouth, MA (US); Douglas Raymond, Bridgewater, MA (US)

(73) Assignee: Medos International Srl, Le Locle (CH)

( * ) Notice: Subject to any disclaimer, the term of this patent is extended or adjusted under 35 U.S.C. 154(b) by 1025 days.

This patent is subject to a terminal disclaimer.

(21) Appl. No.: 17/066,472

(22) Filed: Oct. 8, 2020

(65) Prior Publication Data

US 2021/0059563 A1 Mar. 4, 2021

Related U.S. Application Data

(63) Continuation of application No. 15/263,023, filed on Sep. 12, 2016, now Pat. No. 10,820,835.

(51) Int. Cl.
*A61B 5/00* (2006.01)
*A61B 5/103* (2006.01)
(Continued)

(52) U.S. Cl.
CPC ............ *A61B 5/103* (2013.01); *A61B 5/1072* (2013.01); *A61B 5/1079* (2013.01); *A61B 6/12* (2013.01);
(Continued)

(58) Field of Classification Search
None
See application file for complete search history.

(56) References Cited

U.S. PATENT DOCUMENTS

| 5,156,162 | A | 10/1992 | Gerhardt |
|---|---|---|---|
| 5,251,127 | A | 10/1993 | Raab |

(Continued)

FOREIGN PATENT DOCUMENTS

| CN | 1849101 A | 10/2006 |
|---|---|---|
| CN | 101426455 A | 5/2009 |

(Continued)

OTHER PUBLICATIONS

Australian Office Action for Application No. 2016380934, issued Feb. 5, 2021, (5 pages).

(Continued)

*Primary Examiner* — Michael R Bloch
(74) *Attorney, Agent, or Firm* — Barnes & Thornburg LLP

(57) ABSTRACT

Systems and methods for anatomical alignment are disclosed herein. In some embodiments, the systems and methods can provide accurate and continuous intraoperative validation of anatomical alignment, e.g., of the spine, hips, pelvis, and/or shoulders. An exemplary system can include a sensor and marker arrangement for measuring coronal imbalance. Another exemplary system can include a sensor and marker arrangement for shoulder or pelvic leveling. Yet another exemplary system can include a mechanical frame for establishing a simulated ground plane and projecting a plumb line from the simulated ground plane.

11 Claims, 10 Drawing Sheets

(51) Int. Cl.
*A61B 5/107* (2006.01)
*A61B 6/12* (2006.01)
*A61B 90/00* (2016.01)
*G01C 3/00* (2006.01)

(52) U.S. Cl.
CPC .............. *A61B 90/06* (2016.02); *A61B 90/39* (2016.02); *G01C 3/00* (2013.01); *A61B 2090/061* (2016.02); *A61B 2090/3983* (2016.02); *A61B 2505/05* (2013.01)

(56) References Cited

U.S. PATENT DOCUMENTS

| | | |
|---|---|---|
| 5,291,901 A | 3/1994 | Graf |
| 5,305,203 A | 4/1994 | Raab |
| 5,329,933 A | 7/1994 | Graf |
| 5,748,767 A | 5/1998 | Raab |
| 5,772,610 A | 6/1998 | McGorry et al. |
| 6,015,409 A | 1/2000 | Jackson |
| 6,514,219 B1 * | 2/2003 | Guimond ............ A61B 5/1127 600/595 |
| 6,565,519 B2 | 5/2003 | Benesh |
| 6,711,432 B1 | 3/2004 | Krause et al. |
| 6,715,213 B2 | 4/2004 | Richter |
| 7,001,346 B2 | 2/2006 | White |
| 7,131,952 B1 | 11/2006 | Dickholtz, Sr. et al. |
| 7,139,601 B2 | 11/2006 | Bucholz et al. |
| 7,335,167 B1 | 2/2008 | Mummy |
| 7,559,931 B2 | 7/2009 | Stone |
| 7,611,522 B2 | 11/2009 | Gorek |
| 7,634,119 B2 | 12/2009 | Tsougarakis et al. |
| 7,634,306 B2 | 12/2009 | Sarin et al. |
| 7,706,000 B2 | 4/2010 | Cohen et al. |
| 7,918,887 B2 | 4/2011 | Roche |
| 7,956,887 B2 | 6/2011 | Hoeg et al. |
| 7,957,809 B2 | 6/2011 | Bourget et al. |
| 7,974,677 B2 | 7/2011 | Mire et al. |
| 7,981,115 B2 | 7/2011 | Justis et al. |
| 8,057,479 B2 | 11/2011 | Stone |
| 8,057,482 B2 | 11/2011 | Stone et al. |
| 8,128,662 B2 | 3/2012 | Altarac et al. |
| 8,167,823 B2 | 5/2012 | Nycz et al. |
| 8,348,954 B2 | 1/2013 | Carls et al. |
| 8,442,621 B2 | 5/2013 | Gorek et al. |
| 8,535,337 B2 | 9/2013 | Chang et al. |
| 8,549,888 B2 | 10/2013 | Isaacs |
| 8,565,853 B2 | 10/2013 | Frigg et al. |
| 8,690,888 B2 | 4/2014 | Stein et al. |
| 8,888,821 B2 | 11/2014 | Rezach et al. |
| 9,198,698 B1 | 12/2015 | Doose et al. |
| 9,554,411 B1 | 1/2017 | Hall et al. |
| 9,579,043 B2 | 2/2017 | Chien et al. |
| 9,993,177 B2 | 6/2018 | Chien et al. |
| 10,335,241 B2 | 7/2019 | Frasier et al. |
| 10,396,606 B2 | 8/2019 | Hall et al. |
| 10,499,996 B2 | 12/2019 | de Almeida Barreto |
| 10,714,987 B2 | 7/2020 | Hall et al. |
| 10,743,944 B2 | 8/2020 | Frasier et al. |
| 10,820,835 B2 | 11/2020 | Gupta et al. |
| 11,089,975 B2 | 8/2021 | Frasier et al. |
| 11,160,619 B2 | 11/2021 | Frasier et al. |
| 11,223,245 B2 | 1/2022 | Hall et al. |
| 11,395,604 B2 | 7/2022 | Chien et al. |
| 11,563,345 B2 | 1/2023 | Hall et al. |
| 2002/0035321 A1 | 3/2002 | Bucholz et al. |
| 2002/0120880 A1 | 8/2002 | Simon et al. |
| 2004/0152970 A1 | 8/2004 | Hunter et al. |
| 2005/0033430 A1 | 2/2005 | Powers et al. |
| 2005/0166410 A1 | 8/2005 | Richter et al. |
| 2005/0222793 A1 | 10/2005 | Lloyd et al. |
| 2005/0251026 A1 | 11/2005 | Stone |
| 2005/0262911 A1 | 12/2005 | Dankowicz et al. |
| 2006/0030771 A1 | 2/2006 | Levine et al. |
| 2006/0100508 A1 | 5/2006 | Morrison |
| 2006/0247773 A1 | 11/2006 | Stamp |
| 2007/0060799 A1 | 3/2007 | Lyon et al. |
| 2007/0106146 A1 | 5/2007 | Altmann et al. |
| 2008/0103557 A1 | 5/2008 | Davis et al. |
| 2008/0177203 A1 | 7/2008 | von Jako |
| 2008/0228195 A1 | 9/2008 | von Jako et al. |
| 2008/0266017 A1 | 10/2008 | Simon et al. |
| 2008/0269767 A1 | 10/2008 | O'Brien |
| 2008/0292161 A1 | 11/2008 | Funk et al. |
| 2009/0021752 A1 | 1/2009 | Cohen et al. |
| 2009/0171328 A1 | 7/2009 | Horvath |
| 2009/0249851 A1 | 10/2009 | Isaacs |
| 2010/0010494 A1 | 1/2010 | Quirno |
| 2010/0036384 A1 | 2/2010 | Gorek et al. |
| 2010/0063508 A1 | 3/2010 | Borja et al. |
| 2010/0069919 A1 | 3/2010 | Carls et al. |
| 2010/0087823 A1 | 4/2010 | Kondrashov |
| 2010/0100011 A1 | 4/2010 | Roche |
| 2010/0164296 A1 | 7/2010 | Kurs et al. |
| 2010/0191071 A1 | 7/2010 | Anderson et al. |
| 2010/0191088 A1 | 7/2010 | Anderson et al. |
| 2010/0204575 A1 | 8/2010 | Roche et al. |
| 2010/0204955 A1 | 8/2010 | Roche et al. |
| 2010/0312103 A1 | 12/2010 | Gorek et al. |
| 2011/0040340 A1 | 2/2011 | Miller et al. |
| 2011/0125196 A1 | 5/2011 | Quevedo et al. |
| 2011/0196455 A1 | 8/2011 | Sieracki et al. |
| 2011/0260681 A1 | 10/2011 | Guccione et al. |
| 2011/0270262 A1 | 11/2011 | Justis et al. |
| 2011/0275957 A1 | 11/2011 | Bhandari |
| 2011/0295159 A1 | 12/2011 | Shachar et al. |
| 2012/0035868 A1 | 2/2012 | Roche et al. |
| 2012/0065497 A1 | 3/2012 | Brown et al. |
| 2012/0095330 A1 | 4/2012 | Shechter et al. |
| 2012/0112690 A1 | 5/2012 | Stulen et al. |
| 2012/0123252 A1 | 5/2012 | Brunner |
| 2012/0157019 A1 | 6/2012 | Li |
| 2012/0172653 A1 | 7/2012 | Chornenky et al. |
| 2012/0203140 A1 | 8/2012 | Malchau et al. |
| 2012/0209117 A1 | 8/2012 | Mozes et al. |
| 2012/0232834 A1 | 9/2012 | Roche et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079793 A1 | 3/2013 | Stein et al. |
| 2013/0087950 A1 | 4/2013 | Günther et al. |
| 2013/0131556 A1 | 5/2013 | Chantz |
| 2013/0135312 A1 | 5/2013 | Yang et al. |
| 2013/0165940 A1 | 6/2013 | DiSilvestro |
| 2013/0241468 A1 | 9/2013 | Moshfeghi |
| 2013/0268007 A1 | 10/2013 | Rezach et al. |
| 2013/0303225 A1 | 11/2013 | Maguire |
| 2013/0345718 A1 | 12/2013 | Crawford et al. |
| 2014/0031829 A1 | 1/2014 | Paradis et al. |
| 2014/0052149 A1 | 2/2014 | van der Walt et al. |
| 2014/0057572 A1 | 2/2014 | Klinghult et al. |
| 2014/0088607 A1 | 3/2014 | Recknor |
| 2014/0148808 A1 | 5/2014 | Inkpen et al. |
| 2014/0171965 A1 | 6/2014 | Loh et al. |
| 2014/0232333 A1 | 8/2014 | Kim et al. |
| 2014/0273833 A1 | 9/2014 | McCormack et al. |
| 2014/0273852 A1 | 9/2014 | McCormack et al. |
| 2014/0275940 A1 | 9/2014 | Hladio et al. |
| 2014/0275981 A1 | 9/2014 | Selover et al. |
| 2014/0276871 A1 | 9/2014 | Sherman et al. |
| 2014/0303522 A1 | 10/2014 | Akimoto et al. |
| 2014/0330112 A1 | 11/2014 | Wasielewski |
| 2015/0011874 A1 | 1/2015 | Amoako-Tuffour et al. |
| 2015/0057733 A1 | 2/2015 | Lotfi |
| 2015/0137746 A1 | 5/2015 | Lee et al. |
| 2015/0142372 A1 | 5/2015 | Singh |
| 2015/0150646 A1 | 6/2015 | Pryor et al. |
| 2015/0180263 A1 | 6/2015 | Sud et al. |
| 2015/0185846 A1 | 7/2015 | Otto et al. |
| 2015/0272694 A1 | 10/2015 | Charles |
| 2015/0305786 A1 | 10/2015 | Wehrle et al. |
| 2015/0313482 A1 | 11/2015 | Nabutovsky et al. |
| 2015/0313566 A1 | 11/2015 | Diers et al. |
| 2016/0007909 A1 | 1/2016 | Singh et al. |

(56) References Cited

U.S. PATENT DOCUMENTS

| | | | |
|---|---|---|---|
| 2016/0058320 A1* | 3/2016 | Chien | A61B 5/067 600/424 |
| 2016/0058523 A1 | 3/2016 | Chien et al. | |
| 2016/0191887 A1 | 6/2016 | Casas | |
| 2016/0225192 A1 | 8/2016 | Jones et al. | |
| 2016/0235480 A1 | 8/2016 | Scholl et al. | |
| 2016/0262800 A1 | 9/2016 | Scholl et al. | |
| 2016/0360997 A1 | 12/2016 | Yadav et al. | |
| 2017/0143426 A1 | 5/2017 | Isaacs et al. | |
| 2017/0189121 A1 | 7/2017 | Frasier et al. | |
| 2017/0194820 A1 | 7/2017 | Hall et al. | |
| 2017/0196507 A1 | 7/2017 | Singh et al. | |
| 2017/0231709 A1 | 8/2017 | Gupta et al. | |
| 2017/0348061 A1 | 12/2017 | Joshi et al. | |
| 2018/0070860 A1 | 3/2018 | Gupta et al. | |
| 2018/0256067 A1 | 9/2018 | Chien et al. | |
| 2018/0279913 A1 | 10/2018 | Frasier et al. | |
| 2019/0090955 A1 | 3/2019 | Singh et al. | |
| 2019/0321109 A1 | 10/2019 | Frasier et al. | |
| 2019/0341818 A1 | 11/2019 | Hall et al. | |
| 2020/0297432 A1 | 9/2020 | Frasier et al. | |
| 2020/0303971 A1 | 9/2020 | Hall et al. | |
| 2021/0338107 A1 | 11/2021 | Frasier et al. | |
| 2022/0039877 A1 | 2/2022 | Frasier et al. | |
| 2022/0103024 A1 | 3/2022 | Hall et al. | |
| 2022/0322959 A1 | 10/2022 | Chien et al. | |

FOREIGN PATENT DOCUMENTS

| | | |
|---|---|---|
| CN | 102694421 A | 9/2012 |
| CN | 103385708 A | 11/2013 |
| CN | 103748763 A | 4/2014 |
| CN | 104854533 A | 8/2015 |
| CN | 105011977 A | 11/2015 |
| CN | 105378820 A | 3/2016 |
| EP | 1 943 954 A2 | 7/2008 |
| EP | 2 597 783 A2 | 5/2013 |
| EP | 2 901 957 A1 | 8/2015 |
| GB | 190927693 A | 9/1910 |
| JP | 2000-254141 A | 9/2000 |
| JP | 2003-523795 A | 8/2003 |
| JP | 2005-095433 A | 4/2005 |
| JP | 3746628 B2 | 2/2006 |
| JP | 4323276 B2 | 9/2009 |
| JP | 2009273521 A | 11/2009 |
| JP | 2010-233354 A | 10/2010 |
| JP | 2012120648 A | 6/2012 |
| JP | 2013-544144 A | 12/2013 |
| JP | 2015502766 A | 1/2015 |
| JP | 2015-109785 A | 6/2015 |
| JP | 2015213753 A | 12/2015 |
| JP | 2017510307 A | 4/2017 |
| WO | 1991003980 A1 | 4/1991 |
| WO | 99/15097 A2 | 4/1999 |
| WO | 2005/077000 A2 | 8/2005 |
| WO | 2013/053398 A1 | 4/2013 |
| WO | 2013/169674 A1 | 11/2013 |
| WO | 2014/025305 A1 | 2/2014 |
| WO | 2014/063181 A1 | 5/2014 |
| WO | 2015/003224 A1 | 1/2015 |
| WO | 2015/114119 A1 | 8/2015 |
| WO | 2015/162965 A1 | 10/2015 |
| WO | 2016/032875 A1 | 3/2016 |
| WO | 2019/055912 A1 | 3/2019 |

OTHER PUBLICATIONS

Chinese Office Action for Application No. 201680077321.9, issued Jan. 6, 2021 (17 pages).
Japanese Office Action for Application No. 2018-534634, mailed Nov. 10, 2020 (12 pages).
Mazzilli, F., et al. "Ultrasound Energy Harvesting System for Deep Implanted-Medical-Devices (IMDs)", 2012 IEEE International Symposium on Circuits and Systems (ISCAS),Seoul, 2012, pp. 2865-2868.
Chinese Supplemental Search Report for Application No. 201680077321.9, issued Dec. 5, 2021 (1 page).
Chinese Office Action for Application No. 201780055976.0, issued Mar. 24, 2021 (19 pages).
Chinese Supplemental Search Report for Application No. 201780055976.0, issued Nov. 20, 2021 (1 page).
Japanese Office Action for Application No. 2019-513849, mailed Jun. 8, 2021 (6 pages).
Japanese Office Action for Application No. 2019-553503, mailed Dec. 14, 2021 (10 pages).
Baka, Nora, et al. "2D-3D shape reconstruction of the distal femur from stereo X-ray imaging using statistical shape models," Medical image analysis 15.6 (2011): 840-850.
Conn, K. S., M. T. Clarke, and J.P. Hallett, "A Simple Guide to Determine the Magnification of Radiographs and to Improve the Accuracy of Preoperative Templating," Bone & Joint Journal 84.2 (2002): 269-272.
Delorme, et al., Intraoperative comparison of two instrumentation techniques for the correction of adolescent idiopathic scoliosis. Rod rotation and translation. Spine (Phila Pa 1976). Oct. 1, 1999;24(19):2011-7.
Extended European Search Report for Application No. 17849374.8, dated Mar. 31, 2020 (8 pages).
Ghanem, et al., Intraoperative optoelectronic analysis of three-dimensional vertebral displacement after Cotrel-Dubousset rod rotation. A preliminary report. Spine (Phila Pa 1976). Aug. 15, 1997;22(16):1913-21.
Gorski, J.M., and Schwartz, L. "A Device to Measure X-ray Magnification in Preoperative Planning for Cementless Arthroplasty," Clinical Orthopaedics and Related Research 202 (1986): 302-306.
Australian Office Action for Application No. 2016380934, issued Sep. 16, 2020 (6 pages).
International Search Report and Written Opinion for Application No. PCT/US2015/046217, mailed Nov. 9, 2015 (11 pages).
International Search Report and Written Opinion for Application No. PCT/US2016/067134, mailed Sep. 11, 2017 (20 pages).
International Search Report and Written Opinion for Application No. PCT/US2016/067140, mailed Mar. 23, 2017 (13 pages).
International Search Report and Written Opinion for Application No. PCT/US2017/017344, mailed Jul. 13, 2017 (22 pages).
International Search Report for Application No. PCT/US2017/050023, mailed Jan. 8, 2018 (6 Pages).
International Search Report and Written Opinion for Application No. PCT/US2018/024791, mailed Aug. 6, 2018 (12 pages).
Invitation to Pay Additional Fees for Application No. PCT/US2016/067134, mailed Jun. 26, 2017 (14 pages).
King, R. J., et al. "A Novel Method of Accurately Calculating the Radiological Magnification of the Hip," Bone & Joint Journal 91.9 (2009): 1217-1222.
Lafon, et al., Intraoperative three-dimensional correction during rod rotation technique. Spine (Phila Pa 1976). Mar. 1, 2009;34(5):512-9. doi: 10.1097/BRS.0b013e31819413ec.
Lafon, et al., Intraoperative three dimensional correction during in situ contouring surgery by using a numerical model. Spine (Phila Pa 1976). Feb. 15, 2010;35(4):453-9. doi: 10.1097/BRS.0b013e3181b8eaca. Abstract.
Lamecker, Hans, Thomas H. Wenckebach, and H-C. Hege. ""Atlas-based 3D-shape reconstruction from X-ray images,"" Pattern Recognition, 2006. ICPR 2006. 18th International Conference on. vol. 1. IEEE, 2006; pp. 1-4.
Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.
Mac-Thiong, et al., A new technique for intraoperative analysis of trunk geometry in adolescent idiopathic scoliosis. Can J Surg. Jun. 2002;45(3):219-23.
Mac-Thiong, et al., The effect of intraoperative traction during posterior spinal instrumentation and fusion for adolescent idiopathic scoliosis. Spine (Phila Pa 1976). Jul. 15, 2004;29(14):1549-54.

(56) References Cited

OTHER PUBLICATIONS

Markelj, Primoz, et al. "A review of 3D/2D registration methods for image-guided interventions," Medical image analysis 16.3 (2012): 642-661.
Sarkalkan, Nazli, Harrie Weinans, and Amir A. Zadpoor, "Statistical shape and appearance models of bones," Bone 60 (2014): 129-140.
Schumann, S., Thelen, B., Ballestra, S., Nolte, L. P., Buchler, P., & Zheng, G., "X-ray Image Calibration and Its Application to Clinical Orthopedics," Medical Engineering & Physics (2014): 36(7), 968-974.
The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589.
Written Opinion for Application No. PCT/US2017/050023, mailed Jan. 8, 2018 (4 Pages).
Zheng, Guoyan, et al., "A 2D/3D correspondence building method for reconstruction of a patient-specific 3D bone surface model using point distribution models and calibrated X-ray images," Medical image analysis 13.6 (2009): 883-899.

* cited by examiner

FIG. 6D
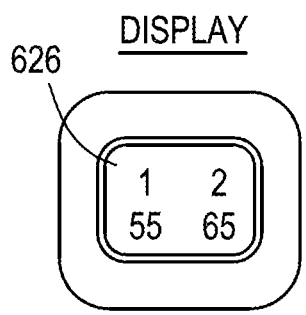
FIG. 6E
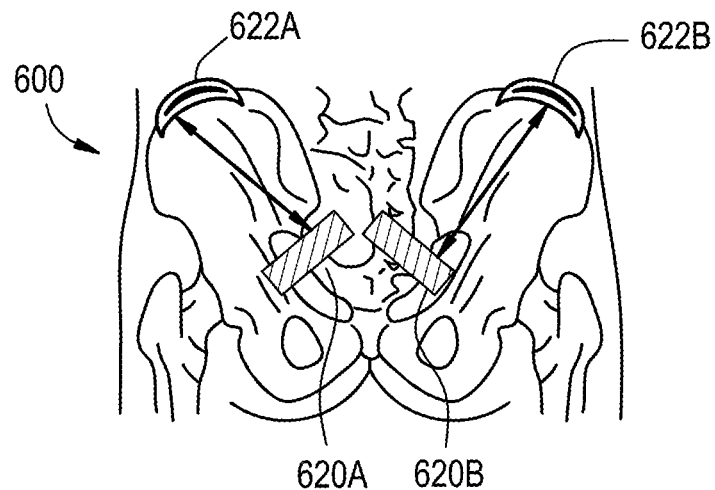
FIG. 6F
FIG. 6G
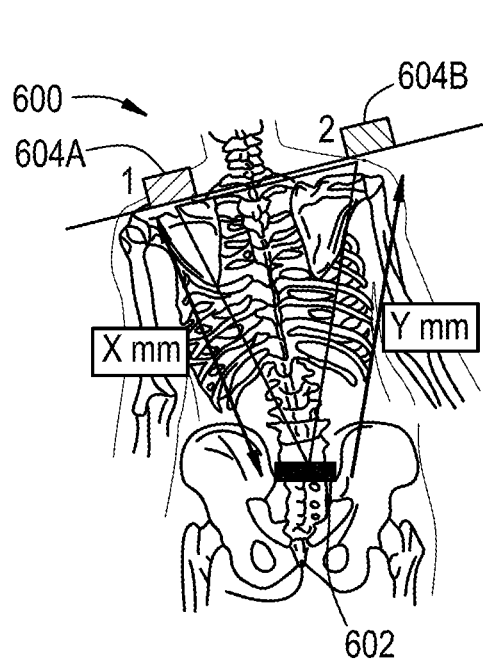
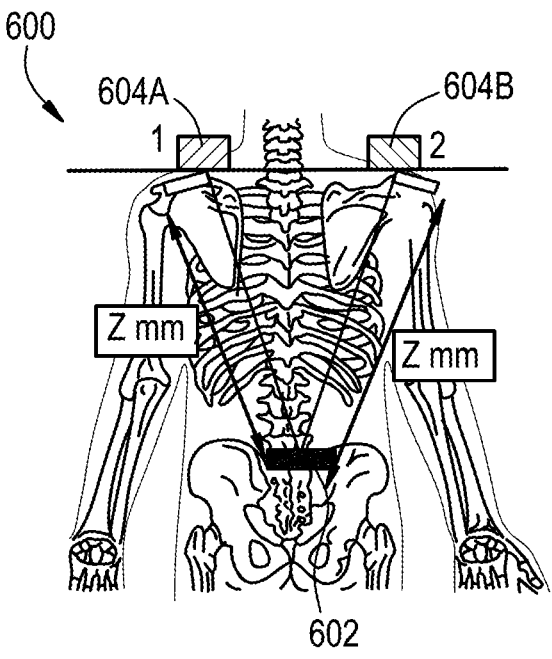

SYSTEMS AND METHODS FOR ANATOMICAL ALIGNMENT

CROSS-REFERENCE TO RELATED APPLICATIONS

This application is a continuation of U.S. application Ser. No. 15/263,023, filed Sep. 12, 2016, which is incorporated herein by reference in its entirety.

FIELD

Systems and methods for anatomical alignment are disclosed herein.

BACKGROUND

Anatomical misalignment is a condition affecting many patients and for which surgical intervention is often required. The misalignment can occur naturally due to age, degenerative conditions, deformities, and so forth. The misalignment can also be caused or exacerbated by a surgical procedure. For example, in spinal surgery, the insertion of a prosthesis or adjustment or removal of bone can result in misalignment of the spine or other anatomical parts of the patient. In some instances, a surgical procedure to correct sagittal balance of the spine can inadvertently cause increased spinal curvature in the coronal plane. In other cases, the shoulders, hips, or pelvis can become unequal, with one side being higher than the other. Misalignment of the spine, hips, pelvis, or shoulders can have serious adverse complications such as poor patient aesthetic index (AI) score, increased wear and tear on patient joints, severe pain, uneven gait, osteoarthritis, and difficulty in performing functions of daily living. Surgical revision is often needed to correct the misalignment.

Anatomical alignment can be difficult to assess and measure during the surgery, though it can be important to do so as this is often the only time that a misalignment can be corrected. Existing techniques for assessing anatomical alignment during surgery typically include use of many cobbled together methods such as "eyeballing," experience, estimation, or use of a manual T-square type device. Current mechanical solutions for estimating alignment tend to be bulky, visually-obstructive to the surgery, cumbersome to use, inaccurate, and usable only with surgical intervention. In addition, such devices do not provide for continuous intraoperative validation. Rather, the surgeon must use their discretion as to when to assess the alignment, which is usually only at a few discrete points during the procedure.

Accordingly, there is a need for improved systems and methods for anatomical alignment.

SUMMARY

Systems and methods for anatomical alignment are disclosed herein. In some embodiments, the systems and methods can provide accurate and continuous intraoperative validation of anatomical alignment, e.g., of the spine, hips, pelvis, and/or shoulders. An exemplary system can include a sensor and marker arrangement for measuring coronal imbalance. Another exemplary system can include a sensor and marker arrangement for shoulder or pelvic leveling. Yet another exemplary system can include a mechanical frame for establishing a simulated ground plane and projecting a plumb line from the simulated ground plane.

In some embodiments, a method for assessing anatomical alignment includes attaching a pointing device to a first location on a patient; attaching a marker to a second location on a patient; and projecting a visual indicator from the pointing device onto a measurement scale of the marker to provide a direct visual indication of an anatomical measurement of the patient.

The first location can be a sacral vertebra and the second location can be a thoracic or cervical vertebra. The anatomical measurement can be a CVA of the patient. Attaching the pointing device can include aligning the visual indicator such that it is parallel to a CSVL of the patient. Attaching the marker can include aligning a measurement axis of the measurement scale such that it is perpendicular to the CSVL of the patient. Attaching the marker can include aligning a measurement axis of the measurement scale such that it is perpendicular to a vertical plumb line extending from the first location.

In some embodiments, a system for assessing anatomical alignment includes a pointing device having an attachment element for attaching the pointing device to a first anatomy of a patient; and a marker having an attachment element for attaching the marker to a second anatomy of the patient, the marker having a measurement scale extending along a measurement axis; wherein the pointing device projects a visual indicator onto the measurement scale, thereby providing a visual indication of an offset between the first anatomy and the second anatomy along the measurement axis.

The pointing device can include a laser pointer. The attachment element of the pointing device can include at least one of a bone pin and a bone anchor. The system can include an alignment guide for aligning at least one of the pointing device and the marker with respect to the patient. The alignment guide can include at least one of a bubble level, an accelerometer, gyroscope, or other sensor, and a beacon or marker for use with a surgical navigation system.

In some embodiments, a method for assessing anatomical alignment includes attaching a first range finder component at a first location on a patient; positioning a second range finder component at a reference axis; attaching a third range finder component at a second location on the patient; positioning a fourth range finder component at the reference axis; measuring a first time of flight between the first and second components; measuring a second time of flight between the third and fourth components; and comparing the first and second times of flight to determine an anatomical measurement of the patient.

The first location can be an inferior vertebra of the patient and the second location can be a superior vertebra of the patient. The anatomical measurement can be a CVA of the patient. The method can include communicating the determined anatomical measurement to a user using at least one of a visual indicator, an audible indicator, a tactile indicator, and an electronic display. The first and second components can be aligned along a first axis that is perpendicular to a CSVL of the patient and the third and fourth components can be aligned along a second axis that is perpendicular to the CSVL of the patient.

In some embodiments, a system for assessing anatomical alignment includes a first range finder including first and second components, the first component having an attachment element for attaching the first component to a first anatomy of a patient, the first range finder configured to measure a first distance between the first and second components; a second range finder including third and fourth components, the third component having an attachment element for attaching the third component to a second anatomy of the patient, the second range finder configured to measure a second distance between the third and fourth components; and a controller configured to compare the first and second distances and to display a difference between the first and second distances on an electronic display.

Each attachment element can include at least one of a bone pin and a bone anchor. The system can include an alignment guide for aligning at least one of the first, second, third, and fourth components with respect to the patient.

In some embodiments, a method for assessing anatomical alignment includes attaching a pointing device at a first location of a patient; attaching a first range finder component at a second location of the patient, the second location being aligned in the coronal plane of the patient with the first location; attaching a second range finder component at a third location of the patient; and measuring a time of flight between first and second range finder components to determine an anatomical measurement of the patient.

The first location can be a sacral vertebra and the third location can be a thoracic or cervical vertebra. The anatomical measurement can be a CVA of the patient. Attaching the pointing device can include aligning a visual indicator emitted by the pointing device such that it is parallel to the CSVL of the patient, the visual indicator being incident upon the first range finder component. Attaching the first and second range finder components can include positioning the first and second components along an axis that is perpendicular to the CSVL of the patient.

In some embodiments, a system for assessing anatomical alignment includes a pointing device having an attachment element for attaching the pointing device to a first anatomy of a patient; a range finder including first and second components, the first component having an attachment element for attaching the first component to a second anatomy of the patient, the second component having an attachment element for attaching the second component to a third anatomy of the patient; the range finder configured to measure a distance between the first and second components; and a controller configured to display the measured distance between the first and second components on an electronic display.

In some embodiments, a method for assessing anatomical alignment includes attaching an imaging device at a first location of a patient; attaching a marker at a second location of the patient, the marker being within a field of view of the imaging device; calibrating the field of view of the imaging device to a reference axis of the patient; and determining from one or more images captured by the imaging device an offset between the marker and the reference axis as an anatomical measurement of the patient.

The first location can be an inferior vertebra and the second location can be a superior vertebra. The anatomical measurement can be a CVA of the patient. The method can include displaying the offset on an electronic display.

In some embodiments, a system for assessing anatomical alignment includes an imaging device configured to capture images of a field of view of the imaging device, the field of view being calibrated to a reference axis of a patient, the imaging device having an attachment element for attaching the imaging device to a first anatomy of the patient; a marker that, when disposed within the field of view of the imaging device, is identifiable in images captured by the imaging device, the marker having an attachment element for attaching the marker to a second anatomy of the patient; and a controller configured to determine from one or more images captured by the imaging device an offset between the marker and the reference axis as an anatomical measurement of the patient, the controller being further configured to display the anatomical measurement on an electronic display.

In some embodiments, a method for assessing anatomical alignment includes attaching a first range finder component at a first location on a patient; attaching a second range finder component at a left anatomy of the patient; attaching a third range finder component at a right anatomy of the patient; measuring a first time of flight between the first and second components; measuring a second time of flight between the first and third components; and comparing the first and second times of flight to determine an anatomical alignment of the left and left anatomies of the patient.

The left and right anatomies can be the patient's left and right shoulders and the anatomical alignment can include a shoulder balance of the patient. The left and right anatomies can be the patient's left and right hips and the anatomical alignment can include a hip balance of the patient. The first component can include a left transceiver aimed towards the second component and a right transceiver aimed towards the third component. The method can include displaying first and second distances represented by the first and second times of flight on an electronic display. The first location can include a vertebra of the patient.

In some embodiments, a method for assessing anatomical alignment includes attaching an imaging device at a first location on a patient; positioning a first marker at a left anatomy of the patient; positioning a second marker at a right anatomy of the patient; determining from one or more images captured by the imaging device a difference between a proximity of the first marker to the imaging device and a proximity of the second marker to the imaging device as an anatomical alignment of the patient.

The imaging device can include an RGB sensor and the first and second markers can include colored flags. The left and right anatomies can be the patient's left and right shoulders and the anatomical alignment can include a shoulder balance of the patient. The left and right anatomies can be the patient's left and right hips and the anatomical alignment can include a hip balance of the patient. The method can include displaying first and second distances represented by the proximities of the first and second markers on an electronic display. The first location can include a vertebra of the patient.

In some embodiments, a method for anatomical alignment includes securing a mechanical frame to a patient at the left and right feet of the patient, the mechanical frame establishing a simulated ground plane; projecting a plumb line from a pointing device mounted to the frame, the plumb line extending perpendicular to the simulated ground plane; and adjusting an anatomy of the patient to the plumb line to correct an anatomical misalignment of the patient.

The method can include using the frame to lock movement of the patient's ankle joints. Adjusting the anatomy of the patient can include bringing the patient's cervico-thoracic junction (CTJ) to the plumb line to balance the patient's shoulders. Adjusting the anatomy of the patient can include bringing the patient's lumbosacral joint L5-S1 to the plumb line to balance the patient's pelvis.

In some embodiments, a system for anatomical alignment includes a mechanical frame configured to be secured to a patient at the left and right feet of the patient; and a pointing device mounted to the frame and configured to project a plumb line therefrom, the plumb line extending perpendicular to a simulated ground plane established by the mechanical frame.

The frame can include attachment features for securing the frame to the patient. The frame can lock movement of the patient's ankle joints.

BRIEF DESCRIPTION OF THE DRAWINGS

FIG. 6D is a top view of a display of the system of FIG. 6A;

FIG. 6E is a top view of the system of FIG. 6A instrumented with a patient's hips;

FIG. 6F is a top view of a patient and a variation of the system of FIG. 6A before shoulder leveling;

FIG. 6G is a top view of a patient and a variation of the system of FIG. 6A after shoulder leveling;

DETAILED DESCRIPTION

Systems and methods for anatomical alignment are disclosed herein. In some embodiments, the systems and methods can provide accurate and continuous intraoperative validation of anatomical alignment, e.g., of the spine, hips, pelvis, and/or shoulders. An exemplary system can include a sensor and marker arrangement for measuring coronal imbalance. Another exemplary system can include a sensor and marker arrangement for shoulder or pelvic leveling. Yet another exemplary system can include a mechanical frame for establishing a simulated ground plane and projecting a plumb line from the simulated ground plane.

Systems and methods herein can provide continuous intraoperative validation of anatomical alignment. Such systems and methods can be actively used without interfering with a surgical procedure. This can allow anatomical alignment to be assessed intraoperatively, while actions can still be taken to correct suboptimal alignment. Systems and methods herein can reduce wound exposure time, reduce the number of steps in the procedure, reduce setup errors, reduce frustration, improve speed, and provide enhanced ease of use.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
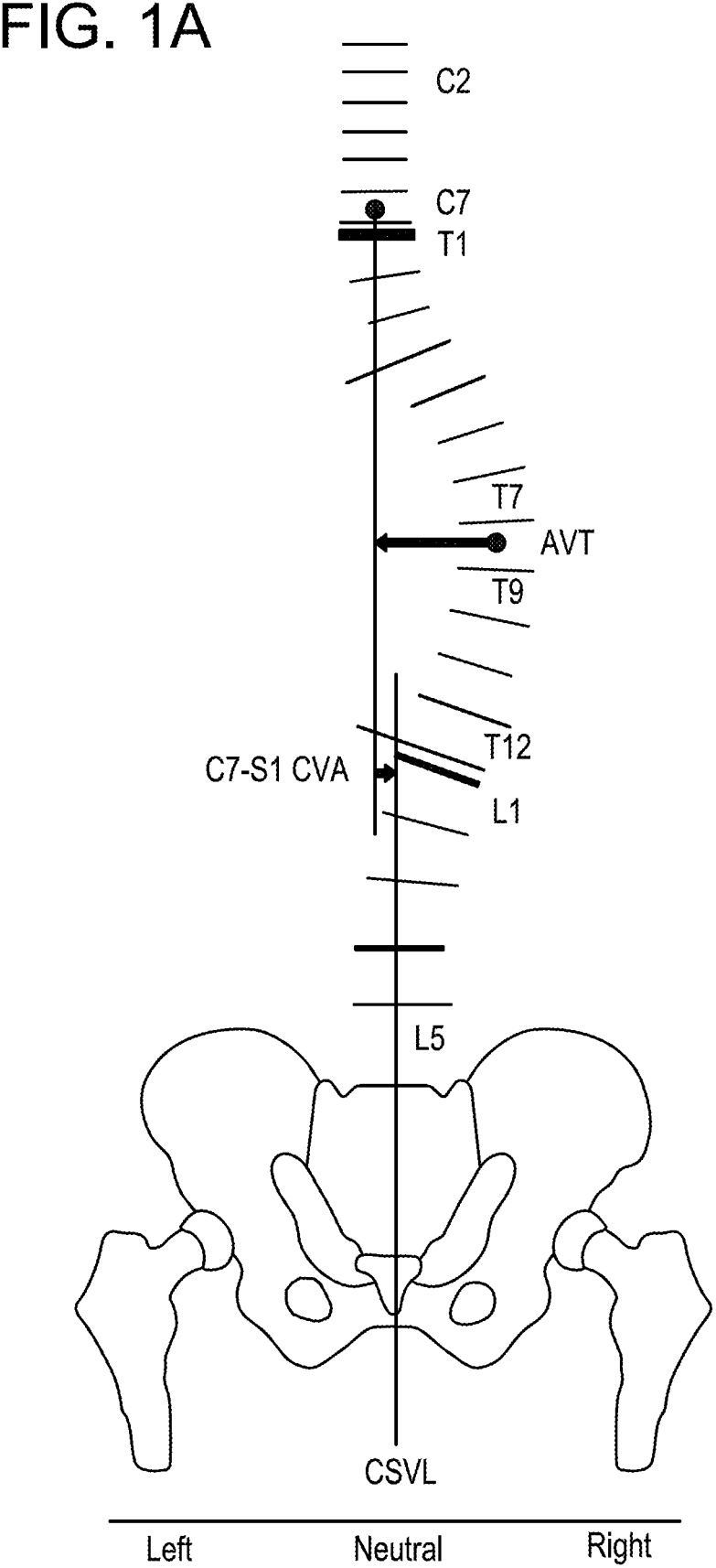
FIG. 1A is a schematic diagram of a misaligned human spine.

FIG. 1A is a schematic diagram of a misaligned human spine. The illustrated spine has a scoliotic curvature defined by an apical vertebral translation (AVT). In addition, the illustrated spine has a coronal imbalance, as defined by an offset in the coronal plane between a vertical plumb line extending from the center of the C7 vertebral body and the central sacral vertical line (CSVL) of the patient. The offset can be referred to as the C7-S1 coronal vertical axis (CVA). In general, it is preferred that the offset be brought as close to zero as possible, with an offset of 2 cm or less typically being considered normal. While the coronal imbalance is measured between C7 and CSVL in the illustrated example, it will be appreciated that the imbalance can exist and/or can be measured from other vertebrae, e.g., other cervical vertebrae, thoracic vertebrae such as T1, or lumbar vertebrae.

Figure 1B:
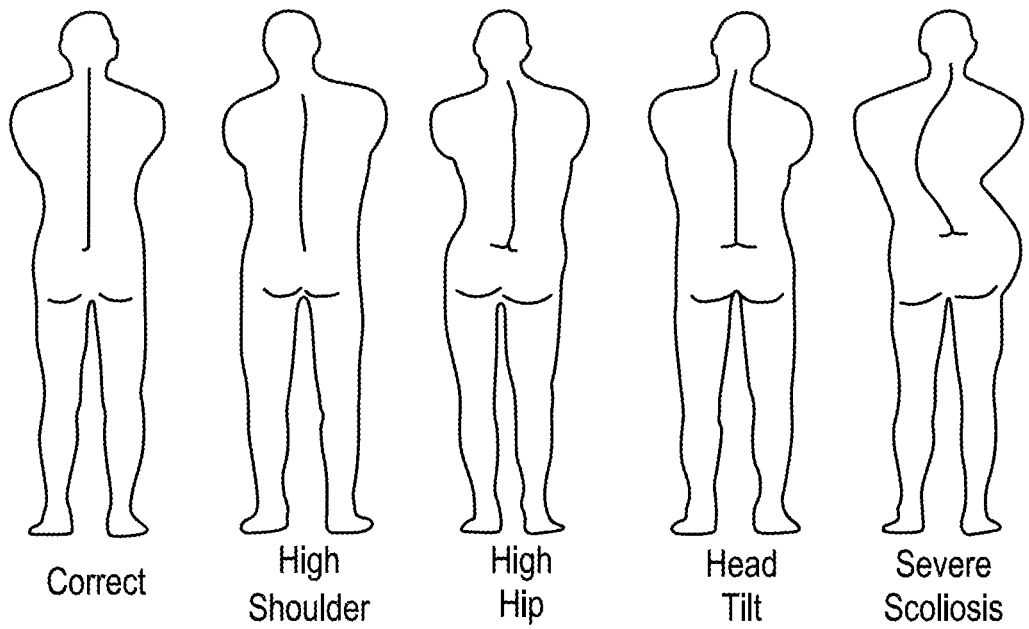
FIG. 1B illustrates a "correct" anatomical alignment along with various anatomical misalignments with which a patient may be afflicted.
Figure 1C:
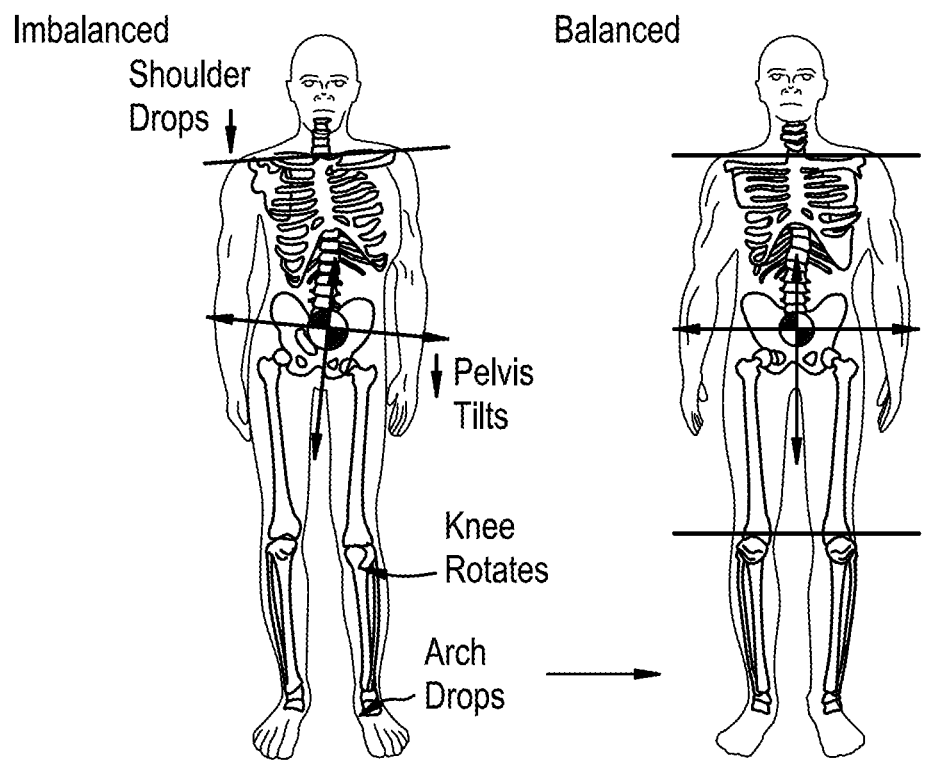
FIG. 1C illustrates an exemplary comparison between a "correct" anatomical alignment and an anatomical misalignment.

FIG. 1B illustrates a "correct" anatomical alignment along with various anatomical misalignments with which a patient may be afflicted. Examples include, from left to right, high shoulder, high hip, head tilt, and severe scoliosis. FIG. 1C illustrates another exemplary comparison between a "correct" or "balanced" anatomical alignment (shown at right with the patient's shoulders, hips, and knees being level) and an anatomical misalignment (shown at left with a dropped shoulder, tilted pelvis, rotated knee, and dropped arch).

Systems and methods herein can measure these and other anatomical alignments, optionally continuously and/or in real time during a surgery to facilitate correction of the alignment.

Figure 2A:
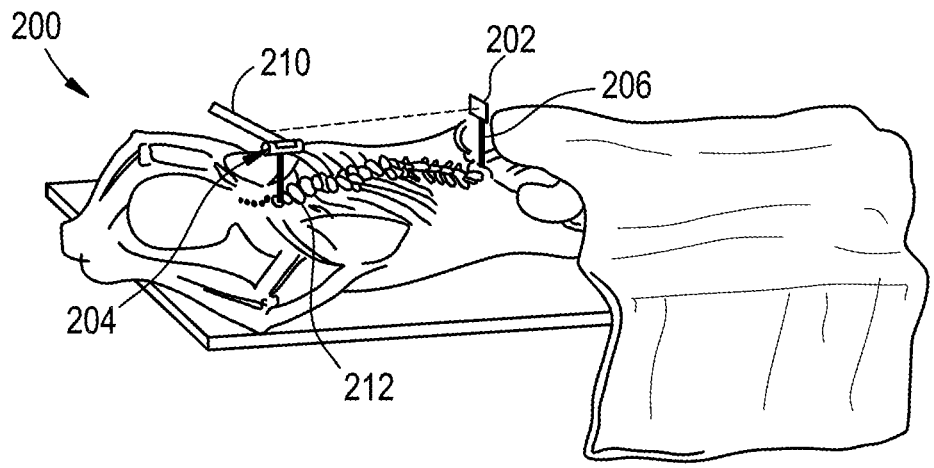
FIG. 2A is a perspective view of a patient instrumented with a system for anatomical alignment.
Figure 2B:
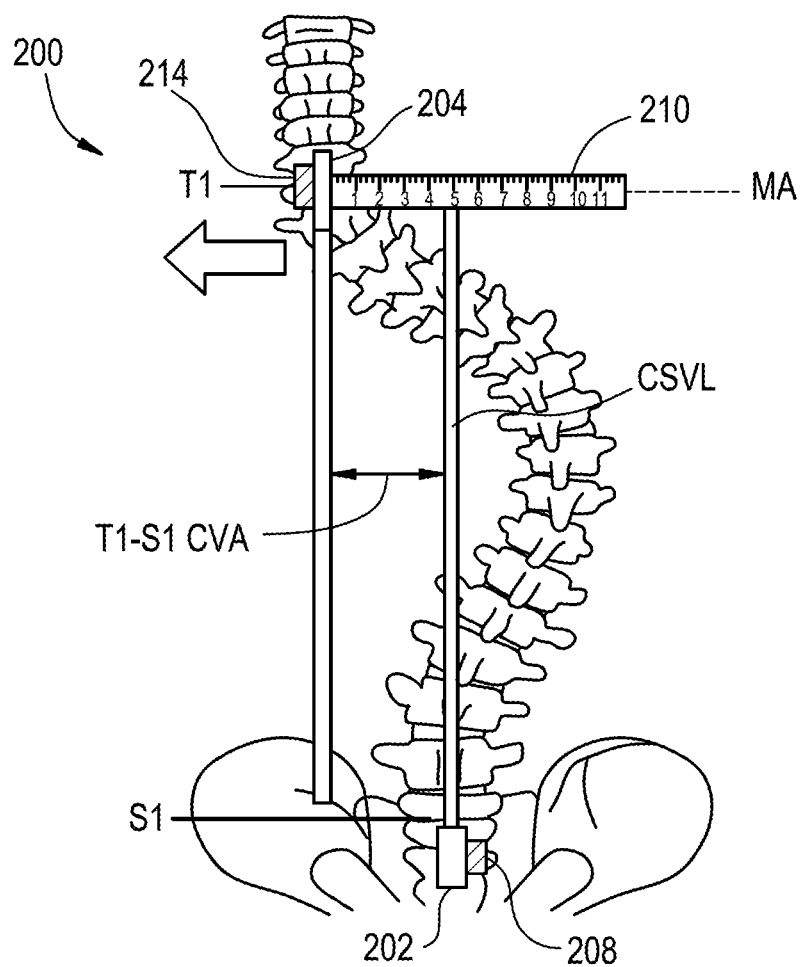
FIG. 2B is a top view of the patient and system of FIG. 2A.

FIGS. 2A-2B illustrate an exemplary system 200 for anatomical alignment that can be used, for example, to measure coronal distance. As shown, the system 200 can include a pointing device 202 and a marker 204.

The pointing device 202 can be configured to project a visual indicator onto the marker 204. The pointing device 202 can include any of a variety of features for projecting the visual indicator, such as a laser, LED pointer, and the like. The pointing device 202 can project the visual indicator in a straight line, e.g., in a line that does not curve in the coronal or sagittal planes.

The pointing device 202 can include an attachment element 206 for attaching the pointing device to the patient. The attachment element 206 can be configured to attach the pointing device 202 to an exterior of the patient, for example using an adhesive, clamp, strap, suture, etc., or can be configured to attach the pointing device to internal anatomy of the patient, for example using a bone pin, bone screw, suture, clamp, etc. The attachment element 206 can be adjustable in one or more degrees of freedom to facilitate alignment of the pointing device 202. In some embodiments, the attachment element 206 allows for six degree-of-freedom adjustment of the pointing device 202 relative to the patient. The attachment element 206 can be lockable in a fixed position such that the pointing device 202 cannot translate or rotate relative to the patient. In some embodiments, multiple bone pins can be used to secure the pointing device 202 to the patient to prevent rotation of the pointing device relative to the patient. The attachment element 206 can support the pointing device 202 in an elevated position to give the pointing device a clear line of sight over the patient's anatomy.

The pointing device 202 can include an alignment guide 208 to assist the user in aligning the pointing device with the patient. For example, the pointing device 208 can include a bubble level, an accelerometer, gyroscope, or other sensor, or a beacon or marker for use with a surgical navigation system. The alignment guide 208 can allow for precise positioning of the pointing device 202 with respect to the patient, e.g., to align the projected visual indicator with an anatomical axis of the patient such as the CSVL. The alignment guide 208 can be omitted and the pointing device 202 can be aligned visually. Alignment of the pointing device 202 can be confirmed using imaging techniques such as fluoroscopy, CT, or MRI.

The marker 204 can include a measurement scale 210. The measurement scale 210 can include indicia or gradations arranged along a measurement axis MA, such as a plurality of numbered lines as shown, to allow visual assessment of distances along the measurement axis. In the illustrated embodiment, the marker 204 includes a single measurement axis MA, aligned for measuring an offset in the coronal plane of the patient. In other embodiments, the measurement axis MA can be aligned for measuring an offset in the sagittal or transverse plane of the patient. In still further embodiments, the measurement scale 210 can include multiple measurement axes, e.g., a first measurement axis for measuring coronal balance and a second measurement axis for measuring sagittal balance. In some embodiments, the measurement scale 210 can include a two-dimensional grid onto which the visual indicator of the pointing device 202 is projected.

The marker 204 can include an attachment element 212 for attaching the marker to the patient. The attachment element 212 can be configured to attach the marker to an exterior of the patient, for example using an adhesive, clamp, strap, suture, etc., or can be configured to attach the marker to internal anatomy of the patient, for example using a bone pin, bone screw, suture, clamp, etc. The attachment element 212 can be adjustable in one or more degrees of freedom to facilitate alignment of the marker 204. In some embodiments, the attachment element 212 allows for six degree-of-freedom adjustment of the marker 204 relative to the patient. The attachment element 212 can be lockable in a fixed position such that the marker 204 cannot translate or rotate relative to the patient. In some embodiments, multiple bone pins can be used to secure the marker 204 to the patient to prevent rotation of the marker relative to the patient. The attachment element 212 can support the marker 204 in an elevated position to give the marker a clear line of sight over the patient's anatomy.

The marker 204 can include an alignment guide 214 to assist the user in aligning the marker with the patient. For example, the marker 204 can include a bubble level, an accelerometer, gyroscope, or other sensor, or a beacon or marker for use with a surgical navigation system. The alignment guide 214 can allow for precise positioning of the marker 204 with respect to the patient, e.g., to align the measurement axis MA such that it is perpendicular to the patient's sagittal plane. The alignment guide 214 can include features for projecting a visual indicator, such as a laser, LED pointer, and the like. As shown, when beam-type indicators are used for the marker 204 and the pointing device 202, proper alignment of the marker and pointing device can be confirmed by comparing the beams to one another and to the sagittal plane of the patient to confirm that the beams and the sagittal plane are each parallel to one another. The alignment guide 214 can be omitted and the marker 204 can be aligned visually. Alignment of the marker 204 can be confirmed using imaging techniques such as fluoroscopy, CT, or MRI.

In use, the pointing device 202 and the marker 204 can be positioned opposite to one another along the patient and can be attached to the patient. In the illustrated embodiment, the pointing device 202 is attached to the patient's S1 vertebra and the marker 204 is attached to the patient's T1 vertebra, though it will be appreciated that the pointing device and marker can be attached at any of a variety of locations on the patient, depending on the measurement of interest.

The alignment guides 208, 214 and attachment elements 206, 212 of the pointing device 202 and the marker 204 can be checked and adjusted as needed to confirm proper alignment. For example, the pointing device 202 can be aligned such that the projected visual indicator is parallel to and in the same sagittal plane as the patient's CSVL and such that the projected visual indicator lands on the measurement scale 210. The marker 204 can be aligned such that the measurement axis MA extends perpendicular to a vertical plumb line extending from the center of T1. Accordingly, the surgeon can quickly assess the patient's T1-S1 CVA by simply observing the location along the measurement scale 210 at which the projected visual indicator lands. The pointing device 202 and the marker 204 can remain attached to the patient as long as desired by the surgeon, and the visual indicator left "on," such that the system 200 can continuously validate coronal balance of the patient's spine. The system 200 can thus provide a continuous, real-time indication to the surgeon of the patient's coronal balance.

It will be appreciated that the positioning of the pointing device 202 and the marker 204 can be reversed. In other words, the pointing device 202 can be attached at a more-superior location on the patient and the marker 204 can be attached at a more-inferior location on the patient. In some embodiments, the pointing device 202 and the marker 204 can be identical components, and thus can be used in either role interchangeably.

In some embodiments, a method for assessing anatomical alignment includes attaching a pointing device to a first location on a patient, attaching a marker to a second location on a patient, and projecting a visual indicator from the pointing device onto a measurement scale of the marker to provide a direct visual indication of an anatomical measurement of the patient. The first position can be the pelvis or an inferior vertebra, the second position can be a superior vertebra, and the anatomical measurement can be a CVA of the patient.

Figure 3A:
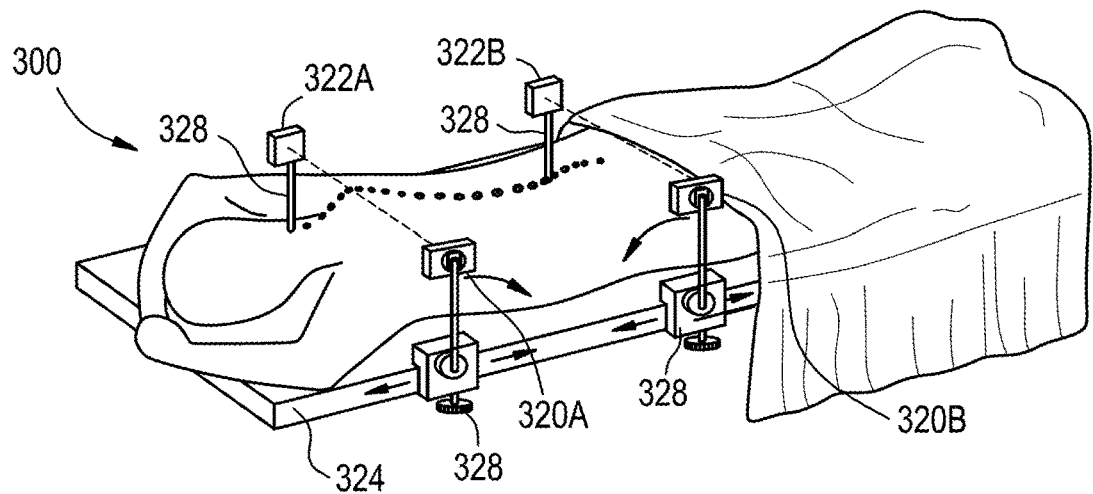
FIG. 3A is a perspective view of a patient instrumented with a system for anatomical alignment.
Figure 3B:
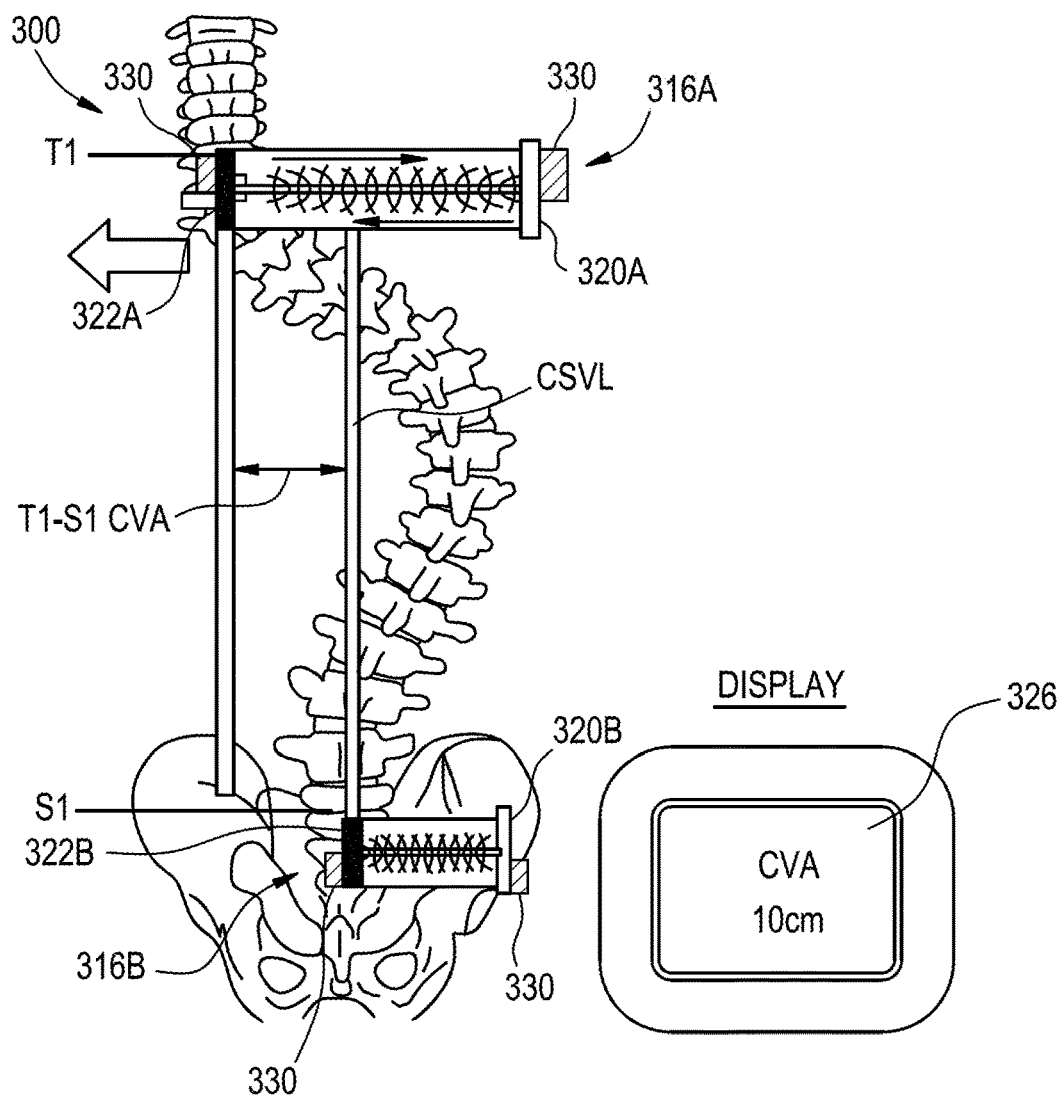
FIG. 3B is a top view of the patient and system of FIG. 3A.

FIGS. 3A-3B illustrate an exemplary system 300 for anatomical alignment that can be used, for example, to measure coronal distance. As shown, the system 300 can include first and second range finder systems 316A, 316B. Each range finder system 316A, 316B can include a transceiver component 320 and a target component 322 and can be configured to measure the range, or distance between the components, e.g., by measuring a time of flight from when an output signal is emitted from the transceiver to when the output signal is reflected off of the target and received back at the transceiver. Exemplary range finders can use optical sensors, pulsed laser sensors, acoustic sensors, or infrared sensors to measure time of flight. In the illustrated embodiment, the system 300 includes two range finders 316, though it will be appreciated that any number of range finders can be used, e.g., to provide redundancy or to measure additional anatomical dimensions. In some embodiments, a single transceiver 320 can be used to measure time of flight to multiple targets 322.

The first and second range finders 316A, 316B can each include a target component 322 mounted to the patient and a transceiver component 320 mounted or positioned along a fixed reference axis, e.g., mounted to the edge of the operating table 324 as shown. In other embodiments, the target component 322 can be positioned along the reference axis and the transceiver component 320 can be mounted to the patient. The first target component 322A can be coupled to a first location on the patient, such as T1, and the second target component 322B can be coupled to a second location on the patient, such as S1. In use, the respective times of flight measured by the transceivers 320A, 320B of the first and second range finders 316A, 316B can be compared to determine a distance between the first and second target components 322A, 322B. For example, the range finders 316 can measure the relative distance between the target components 322 in the coronal plane which, in the example above, is commensurate with the T1-S1 CVA of the patient. In the illustrated embodiment, the targets 322 are attached to the patient's S1 and T1 vertebrae, though it will be appreciated that the targets can be attached at any of a variety of locations on the patient, depending on the measurement of interest. In some embodiments, the transceivers 320 and the targets 322 can be identical components, and thus can be used in either role interchangeably.

The system 300 can include an indicator for communicating the measured distance to the surgeon. For example, the system 300 can include a controller that drives an electronic display 326 to graphically display the relative distance to the surgeon. By way of further example, the system can emit audible, visual, and/or tactile feedback when the relative distance is within an acceptable range, e.g., when the measured CVA is within a predetermined distance of zero, such as +/−2 cm, or when the relative distance is outside of an acceptable range. The feedback can be emitted by a light such as an LED, a speaker, a buzzer, a vibrator, etc.

The transceiver and/or target components of the range finders 316 can include an attachment element 328 for attaching the component to the patient or to a fixed reference point, as the case may be. The attachment element 328 can be configured to attach the component to an exterior of the patient, for example using an adhesive, clamp, strap, suture, etc., or can be configured to attach the component to internal anatomy of the patient, for example using a bone pin, bone screw, suture, clamp, etc. The attachment element 328 can be adjustable in one or more degrees of freedom to facilitate alignment of the range finder components. In some embodiments, the attachment element 328 allows for six degree-of-freedom adjustment of the component relative to the patient or reference point. The attachment element 328 can be lockable in a fixed position such that the component cannot translate or rotate relative to the patient or reference point. In some embodiments, multiple bone pins can be used to secure the component to the patient to prevent rotation of the component relative to the patient. The attachment element 328 can support the component in an elevated position to give the component a clear line of sight over the patient's anatomy.

The transceiver and/or target components of the range finders 316 can include an alignment guide 330 to assist the user in aligning the components with the patient, with the reference axis, and with each other. For example, the components can include a bubble level, an accelerometer, gyroscope, or other sensor, or a beacon or marker for use with a surgical navigation system. The alignment guide 330 can allow for precise positioning of the components with respect to the patient and the reference axis, e.g., to align the incident path and reflected path of the emitted signals such that they are perpendicular to the sagittal plane, plumb line, or CSVL of the patient and to the reference axis. The alignment guide 330 can be omitted and the components can be aligned visually. Alignment of the components can be confirmed using imaging techniques such as fluoroscopy, CT, or MRI. In some embodiments, one or both components of the range finders 316 can be configured to project a visual indicator onto the opposite component. The components can include any of a variety of features for projecting the visual indicator, such as a laser, LED pointer, and the like. The component can project the visual indicator in a straight line, e.g., in a line that does not curve in the coronal or sagittal planes. The projected visual indicators can be used to confirm alignment between the transceiver and target.

In use, the targets 322 can be attached to the patient and the transceivers 320 can be attached along the reference axis, or vice versa. The alignment guides 330 and attachment elements 328 of the range finder components can be checked and adjusted as needed to confirm proper alignment. The times of flight measured by the range finders 316 can be compared, e.g., using a processor, controller, computer system, etc., to determine a relative distance between the targets 322 and therefore determine an anatomical measurement of the patient. For example, the range finders 316 can measure the relative distance between the target components 322 in the coronal plane which, in the example above, is commensurate with the T1-S1 CVA of the patient. The anatomical measurement can be communicated to the surgeon such that the surgeon can quickly assess the measurement in real time and continuously throughout the surgery.

In some embodiments, a method for assessing anatomical alignment can include attaching a first range finder component at a first location on a patient, positioning a second range finder component at a reference axis, attaching a third range finder component at a second location on the patient, positioning a fourth range finder component at the reference axis, measuring a first time of flight between the first and second components, measuring a second time of flight between the third and fourth components, and comparing the first and second times of flight to determine an anatomical measurement of the patient. The first location can be the pelvis or an inferior vertebra, the second location can be a superior vertebra, and the anatomical measurement can be a CVA of the patient. The method can include communicating the determined anatomical measurement to a user using at least one of a visual indicator, an audible indicator, a tactile indicator, and an electronic display.

Figure 4A:
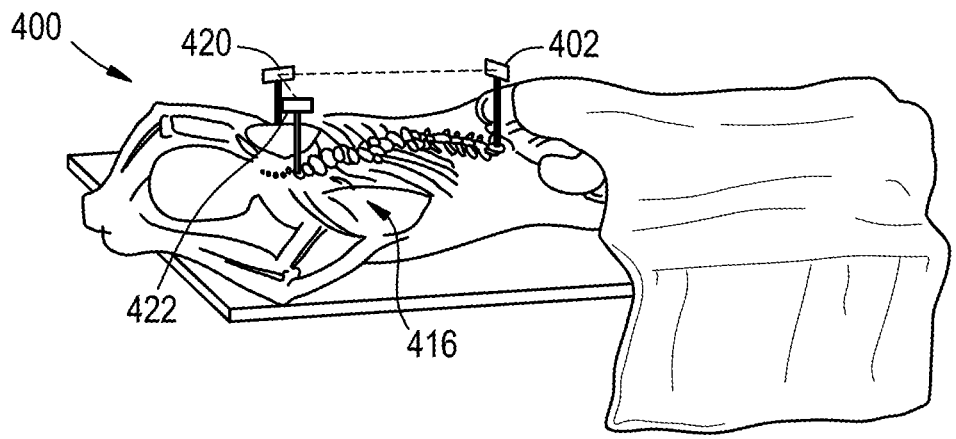
FIG. 4A is a perspective view of a patient instrumented with a system for anatomical alignment.
Figure 4B:
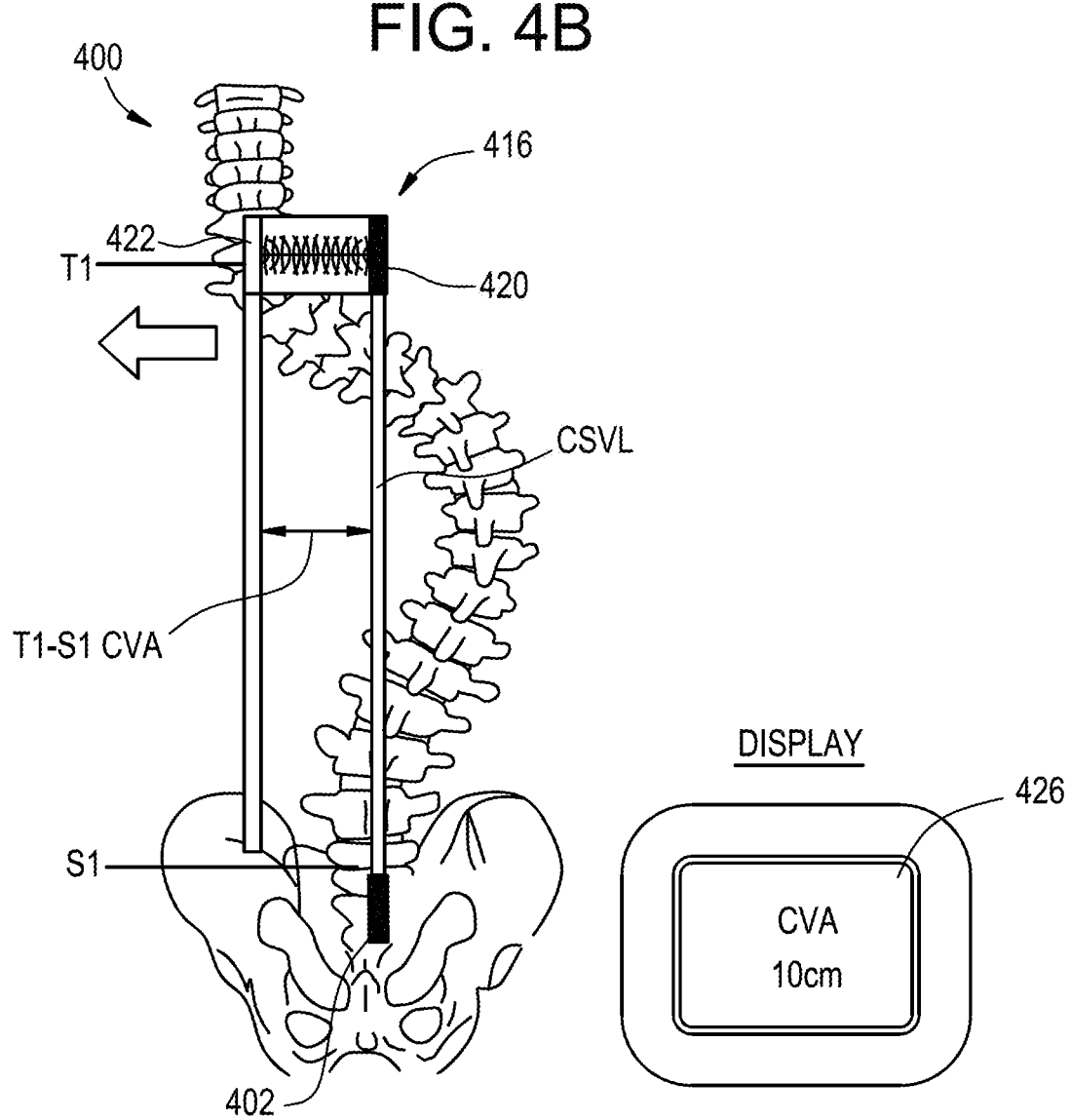
FIG. 4B is a top view of the patient and system of FIG. 4A.

FIGS. 4A-4B illustrate an exemplary system 400 for anatomical alignment that can be used, for example, to measure coronal distance. As shown, the system 400 can incorporate features of the systems 200, 300 described above. In particular, the system 400 can include a pointing device 402 and a range finder 416 having a transceiver component 420 and a target component 422. The pointing device 402 can be attached to the patient as in the pointing device 202 in the system 200 above, and one of the range finder components 422 can be attached to the patient as in the marker 204 in the system 200 above. The other range finder component 420 can be held by the user or attached to the patient at a location offset laterally from the first range finder component 422, as determined by the visual indicator projected from the pointing device 402. In other words, the range finder target component 422 can be attached to T1, and the range finder transceiver component 420 can be positioned opposite the target at a location where the projected visual indicator of the pointing device 402 is incident on the transceiver. The opposite arrangement can also be used, i.e., in which the transceiver 420 is attached to the patient and the target 422 is aligned with the pointing device 402. The range finder 416 can then measure the time of flight between the transceiver 420 and the target 422 and thereby determine the relative distance between the two. In the illustrated embodiment, the relative distance between the transceiver 420 and the target 422 equates to the T1-S1 CVA of the patient. It will be appreciated that the illustrated attachment points are merely exemplary and that the system 400 can be used to determine any of a variety of anatomical measurements of the user. In the system 400, the range finder 416 measures the target dimension directly, as opposed to comparing first and second times of flight as in the system 300 above. The determined anatomical measurement can be communicated to the user as described above, for example using an electronic display 426.

In some embodiments, a method for assessing anatomical alignment can include attaching a pointing device at a first location of a patient, attaching a first range finder component at a second location of the patient, the second location being aligned in the coronal plane of the patient with the first location, attaching a second range finder component at a third location of the patient, and measuring a time of flight between first and second range finder components to determine an anatomical measurement of the patient.

Figure 5A:
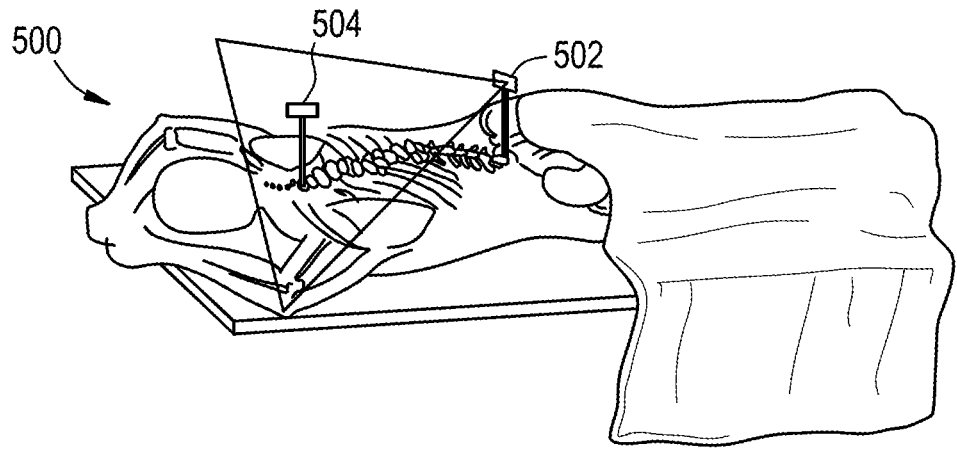
FIG. 5A is a perspective view of a patient instrumented with a system for anatomical alignment.
Figure 5B:
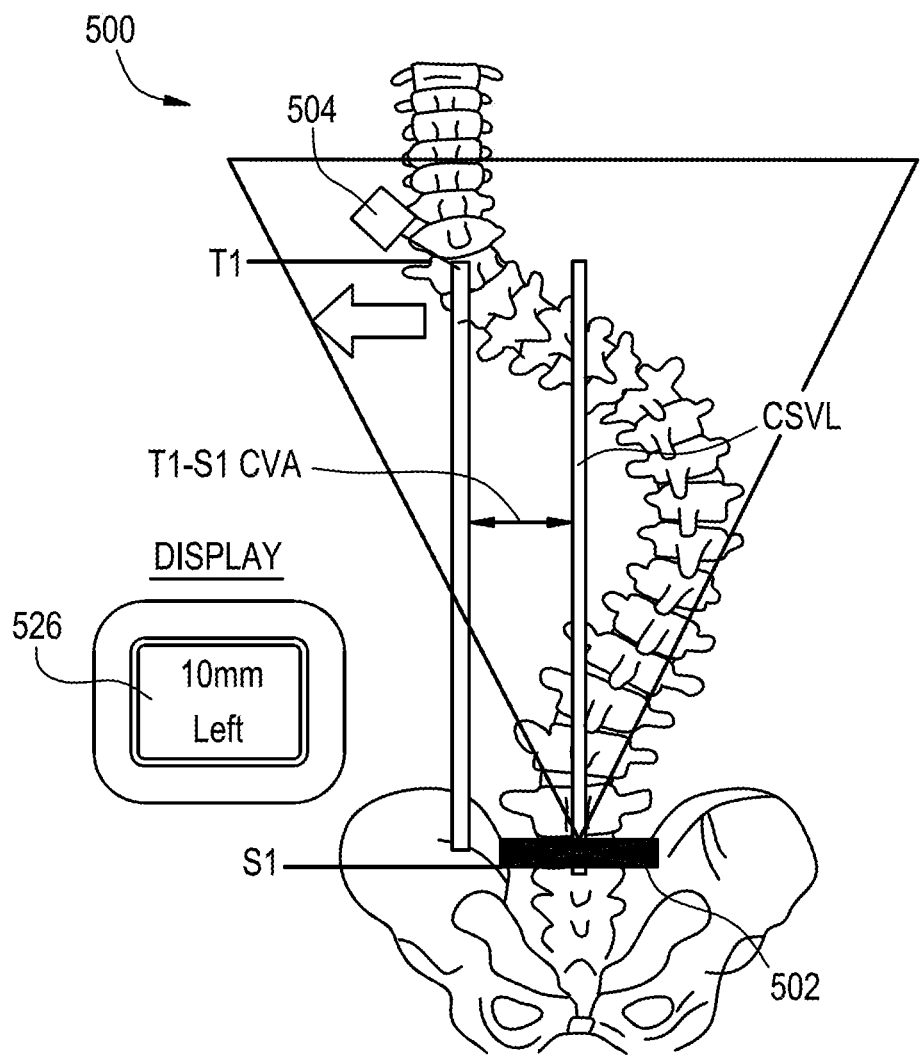
FIG. 5B is a top view of the patient and system of FIG. 5A.

FIGS. 5A-5B illustrate an exemplary system 500 for anatomical alignment that can be used, for example, to measure coronal distance. Except as indicated below and as will be readily apparent to one having ordinary skill in the art, the structure and operation of the system 500 is substantially identical to that of the system 200 described above, and therefore a detailed description is omitted here for the sake of brevity. The system 500 and the components thereof can include any of the features of the systems described above, including attachment features, alignment guides, and the like.

In the system 500, an imaging device 502 is used in place of the pointing device 202 of the system 200 and a marker 504 having a predetermined color, marking, pattern, etc. is used in place of the marker 204 of the system 200. The field of view of the imaging device can be aligned, calibrated, or registered to the CSVL or other reference axis of interest of the patient, such that a location of the marker 504 relative to the reference axis can be determined from the captured image. For example, the imaging device 502 can be marked with a radiopaque line to denote the central axis of the image sensor, and the line can be aligned with the reference axis of the patient using fluoroscopy. By way of further example, anatomical landmarks of the patient, such as the median sacral crest or a spinous process of a lumbar vertebra, can be identified within the captured image to locate the reference axis. As yet another example, the imaging device 502 can be aligned visually. A controller can execute an image processing routine to identify the marker 504 within the captured image and to calculate an offset between the marker and the reference axis, thereby calculating an anatomical measurement of the patient, e.g., a T1-S1 CVA as shown.

Any of a variety of known imaging devices 502 can be used, including CCD, CMOS, or NMOS image sensors, photodiodes, optical sensors, video tracker sensors, video surface sensors, fiber optic sensors, laser scan sensors, electromagnetic sensors, combinations of sensors described herein, and so forth. In some embodiments, the imaging device 502 can be a RGB sensor, e.g., a commercially available RGB-D sensor. The marker 504 can be colored red, green, or blue to facilitate recognition by the RGB sensor.

The determined anatomical measurement can be communicated to the user as described above, for example using an electronic display 526 as shown. The electronic display can be integral with the image sensor 502 or part of a remote computer system. The system 500 can communicate the offset to the user along with the direction of the offset, e.g., left or right as shown.

FIGS. 6A-6G illustrate an exemplary system 600 for anatomical alignment that can be used, for example, for shoulder and/or pelvic leveling.

Figure 6A:
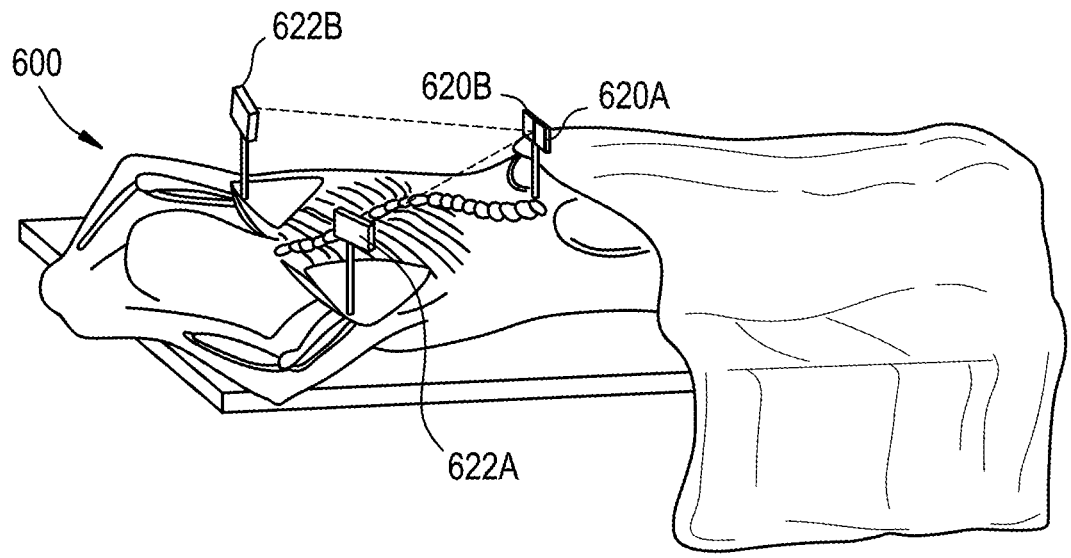
FIG. 6A is a perspective view of a system for anatomical alignment instrumented with a patient's shoulders.
Figure 6B:
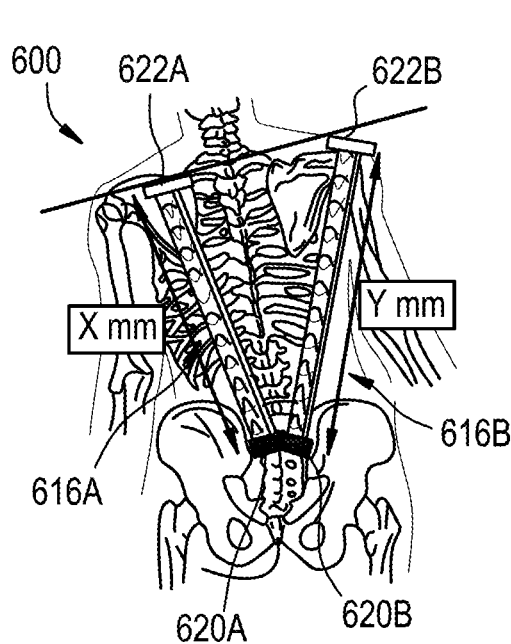
FIG. 6B is a top view of the patient and system of FIG. 6A before shoulder leveling.
Figure 6C:
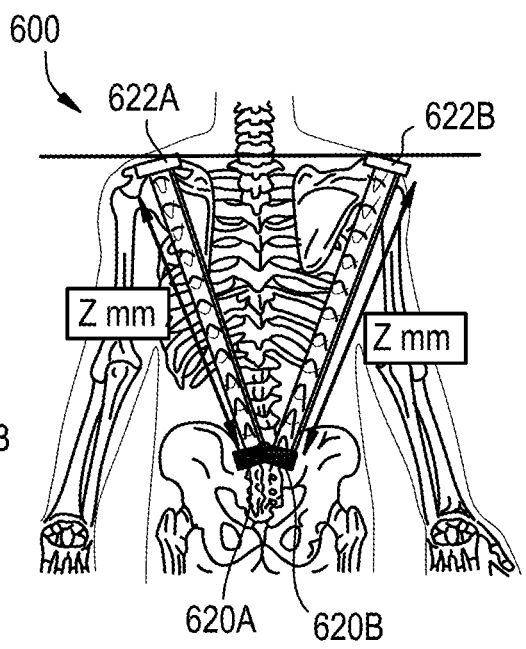
FIG. 6C is a top view of the patient and system of FIG. 6A after shoulder leveling.

As shown in FIGS. 6A-6C, the system 600 can include left and right range finders 616A, 616B. The left range finder 616A can include a transceiver component 620A and a target component 622A, and the right range finder can include a transceiver component 620B and a target component 622B. The range finders 616 can include any of the features of the range finders described above, including attachment elements, alignment guides, and so forth. In some embodiments, a single transceiver component 620 can measure times of flight to multiple target components 622.

In use, the times of flight measured by the range finders 616A, 616B can be compared, e.g., using a processor, controller, computer system, etc. to determine a relative distance between the targets 622A, 622B and therefore determine an anatomical measurement of the patient. The anatomical measurement can be communicated to the surgeon such that the surgeon can quickly assess the measurement in real time and continuously throughout the surgery.

In the illustrated embodiment, the range finder transceivers 620A, 620B are attached to the patient's S1 vertebra and the range finder targets 622A, 622B are attached to the patient's left and right shoulders, respectively, for example to the superior angle of the left scapula and the superior angle of the right scapula. The difference in time of flight measured by the left and right range finders 616A, 616B can thus indicate an amount of shoulder imbalance in the patient. As shown in FIG. 6B, a distance X represented by the time of flight measured by the left range finder 616A differs from a distance Y represented by the time of flight measured by the right range finder 616B when the patient's shoulders are unbalanced. As shown in FIG. 6C, the distances Z represented by the times of flight measured by the left and right range finders 616A, 616B are equal or substantially equal when the patient's shoulders are balanced or level. The distances measured by the left and right range finders 616A, 616B can be communicated to the surgeon, for example using an electronic display 626 as shown in FIG. 6D. The location on the display at which the measurement is shown can be coordinated with the location on the patient on which the range finder is mounted. For example, a measurement obtained from the left range finder 616A can be displayed on a left side of the display 626 and a measurement obtained using the right range finder 616B can be displayed on a right side of the display. Thus, in the illustrated example, the surgeon can readily observe from the display 626 that the left shoulder is 10 cm lower than the right shoulder.

The system 600 can be used to measure other anatomical alignments of the patient, such as hip or pelvis balance as shown in FIG. 6E. As shown, the range finder targets 622A, 622B can be attached to the patient's hips, for example at the outer edge of the iliac crest. The system 600 can be used as described above to convey to the surgeon the degree of balance or imbalance of the patient's pelvis.

While a range finder arrangement is shown and described above, it will be appreciated that the system 600 can use other measurement technology instead or in addition. For example, as shown in FIGS. 6F-6G, the system 600 can include an imaging device 602 of the type described above and left and right markers 604A, 604B configured to be detected in images captured by the imaging device. In some embodiments, the imaging device 602 can be an RGB sensor and the markers 604A, 604B can have different colors, e.g., one blue and one green, to make them easily distinguishable by the RGB sensor. In use, image data captured by the image sensor 602 can be processed to determine the relative proximity of the left and right markers 604A, 604B to the imaging device. For example, the size of the markers 604A, 604B within the captured image can be determined to assess the proximity of the markers. As shown in FIG. 6F, the proximity X of the left marker 604A differs from the proximity Y of the right marker 604B when the patient's shoulders are unbalanced. As shown in FIG. 6G, the proximity Z of the left and right markers 604A, 604B is equal or substantially equal when the patient's shoulders are balanced or level. The system 600 shown in FIGS. 6F-6G can also be used for pelvic leveling or for assessing other anatomical alignment. Any of a variety of known imaging devices 602 can be used, including CCD, CMOS, or NMOS image sensors, photodiodes, optical sensors, video tracker sensors, video surface sensors, fiber optic sensors, laser scan sensors, electromagnetic sensors, combinations of sensors described herein, and so forth.

Figure 7A:
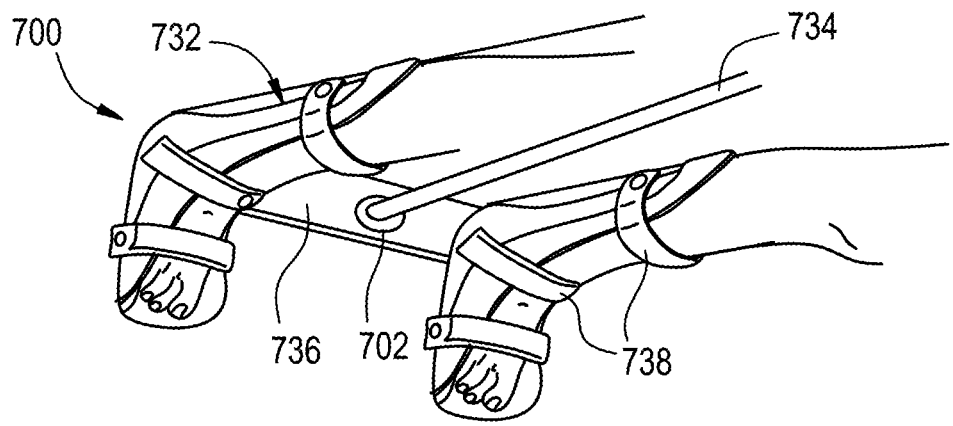
FIG. 7A is a perspective view of a patient instrumented with a system for anatomical alignment.
Figure 7B:
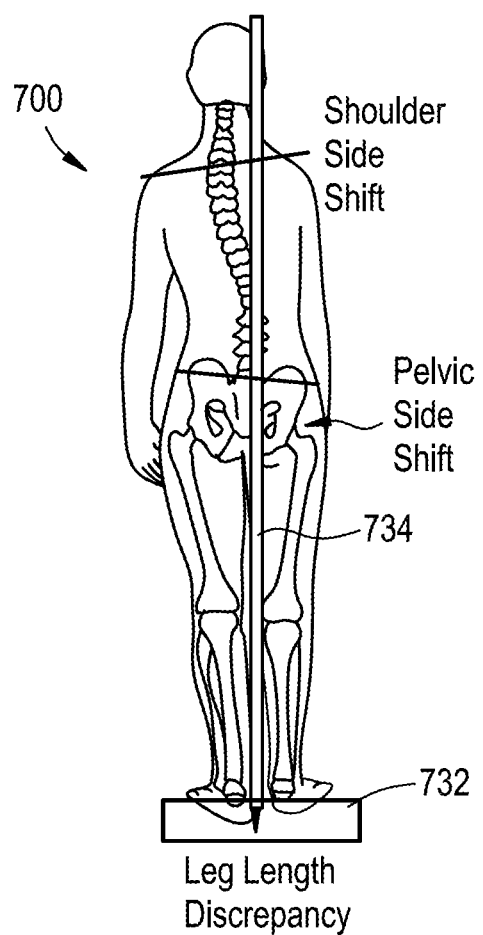
FIG. 7B is a top view of the patient and system of FIG. 7A.

FIGS. 7A-7B illustrate an exemplary system 700 for anatomical alignment that can be used, for example, for shoulder and/or pelvic leveling, especially in patients with leg length discrepancy. As shown, the system 700 can include a mechanical frame 732 for establishing a simulated ground plane with respect to the patient, for example when the patient is lying on the operating table. The frame 732 can include a pointing device 702, e.g., of the type described above, configured to project a visual indicator. The pointing device can include any of a variety of features for projecting the visual indicator, such as a laser, LED pointer, and the like. The pointing device 702 can project the visual indicator in a straight line, e.g., in a line that does not curve in the coronal or sagittal planes. In the illustrated embodiment, the pointing device 702 projects a light beam 734 that acts as a plumb line which is perpendicular to the simulated ground plane of the frame 732. Accordingly, the frame 732 can be attached to the patient and various portions of the patient's anatomy can be compared to the plumb line 734 to assess alignment. As shown in FIG. 7B, a patient with a leg length discrepancy can present with a pelvic side shift and a shoulder side shift as compared to the plumb line 734. The surgeon can correct the misalignment, for example by bringing the patient's cervico-thoracic junction (CTJ) to the plumb line 734 to balance the shoulders and/or by bringing the patient's lumbosacral joint L5-S1 to the plumb line 734 to balance the pelvis.

The frame 732 can be secured to the patient at any of a variety of locations. In the illustrated embodiment, the frame 732 is secured to the patient's lower extremities with a foot plate 736 pressed firmly against the patient's heels. The foot plate 736 can thus define a simulated ground plane that intersects with the left and right heels of the patient. The frame 732 can include straps or other attachment features 738 for securing the frame to the patient. The frame 732 can be configured to lock or restrict movement of one or more of the patient's joints. In the illustrated embodiment, the frame 732 locks out the patient's ankle joints. In other embodiments, the frame 732 can lock out other joints of the patient instead or in addition, such as the knee joints, hip joints, etc.

Any one or more of the systems described above can include a controller, data processor, or computer system, e.g., for processing sensor outputs or captured images, comparing measured ranges, calculating anatomical alignments, displaying an anatomical measurement to a user, and so forth.

Figure 8:
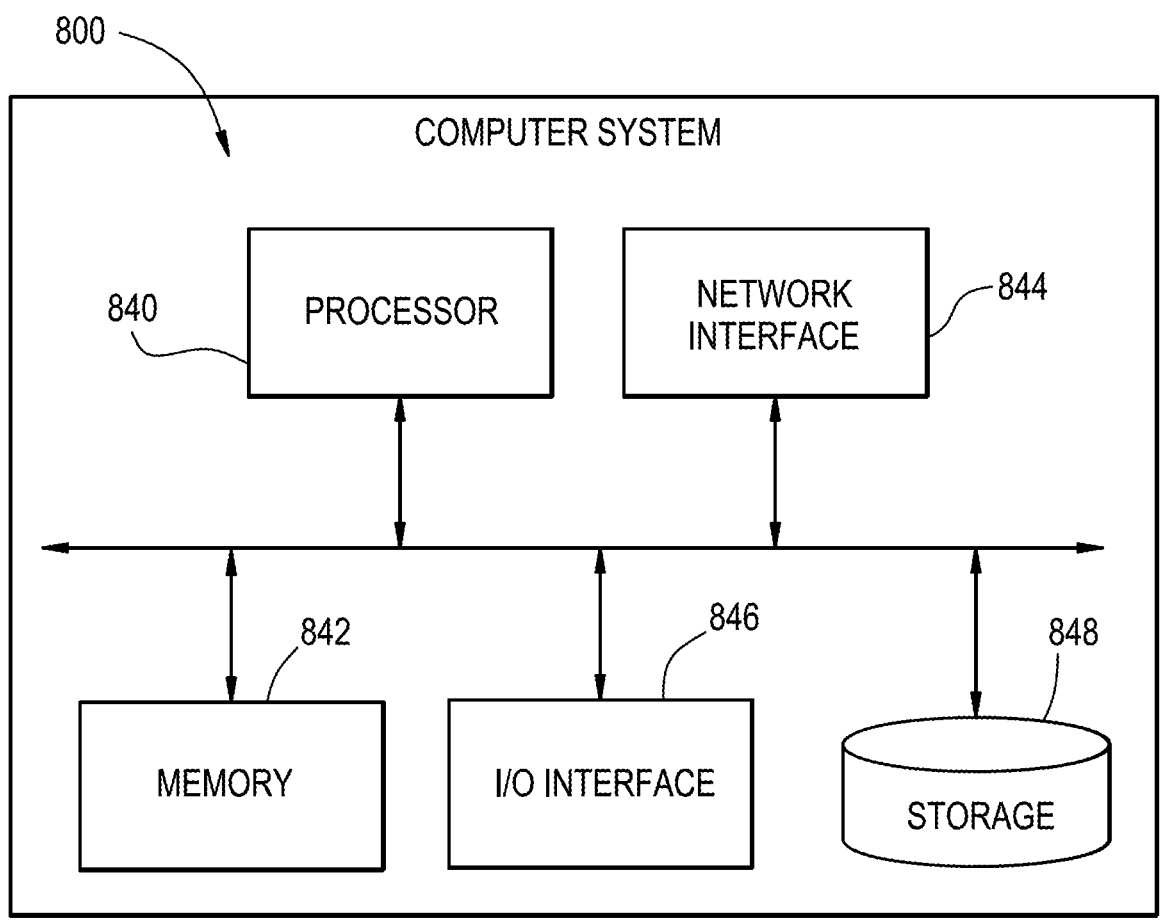
FIG. 8 is a schematic diagram of a computer system that can be used with the systems above.

FIG. 8 illustrates an exemplary computer system 800 that can be used with any of the anatomical alignment systems described above. While an exemplary computer system 800 is depicted and described herein, it will be appreciated that this is for sake of generality and convenience. In other embodiments, the computer system 800 may differ in architecture and operation from that shown and described here. The computer system 800 can be a tablet computer, mobile device, smart phone, laptop computer, desktop computer, cloud-based computer, server computer, and so forth. Software can execute on the computer system 800. The software can execute on a local hardware component (e.g., a tablet computer, smart phone, laptop computer, or the like) or can execute remotely (e.g., on a server or cloud-connected computing device in communications coupling with the computer system 800). The computer system 800 can be physically or communicatively connected, e.g., in real-time, with other software or hardware systems, including Software as a Medical Device (SaMD), pre-operative planning software, a Picture Archiving and Communication System (PACS), an Electronic Medical Record (EMR) system, an Electronic Health Record (EHR) system, and/or an electronic Patient-Reported Outcome (ePRO) system. The computer system 800 can be connected to such other systems for data transfer, data analytics, machine learning, and/or real-time prescriptive clinical decision making for surgical intervention and correction.

The illustrated computer system 800 includes a processor 840 which controls the operation of the computer system, for example by executing embedded software, operating systems, device drivers, application programs, and so forth. The processor 840 can include any type of microprocessor or central processing unit (CPU), including programmable general-purpose or special-purpose processors. As used herein, the term processor can refer to microprocessors, microcontrollers, ASICs, FPGAs, PICs, processors that read and interpret program instructions from internal or external memory or registers, and the like. The computer system 800 also includes a memory 842, which provides temporary or permanent storage for code to be executed by the processor 840 or for data that is processed by the processor. The memory 842 can include read-only memory (ROM), flash memory, one or more varieties of random access memory (RAM), and/or a combination of memory technologies. The various components of the computer system 800 can be interconnected via any one or more separate traces, physical busses, communication lines, etc.

The computer system 800 can also include a communication or network interface 844 and an I/O interface 846.

The network interface 844 can enable the computer system 800 to communicate with remote devices (e.g., other computer systems) over a network or communications bus (e.g., a universal serial bus). The I/O interface 846 can facilitate communication between one or more input devices, one or more output devices, and the various other components of the computer system 800. Exemplary input or output devices include electronic displays, touch screens, mechanical buttons, keyboards, pointing devices, and anatomical alignment sensors or components (e.g., pointing devices, range finders, and imaging devices of the type described above). The computer system 800 can also include a storage device 848, which can include any conventional medium for storing data in a non-volatile and/or non-transient manner. The storage device 848 can include one or more hard disk drives, flash drives, USB drives, optical drives, various media disks or cards, and/or any combination thereof and can be directly connected to the other components of the computer system 800 or remotely connected thereto, such as through the communication interface 844. The elements illustrated in FIG. 8 can be some or all of the elements of a single physical machine. In addition, not all of the illustrated elements need to be located on or in the same physical machine.

The various functions performed by the computer system 800 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the systems and methods illustrated and described herein generally involve assessing alignment of the spine, hips, or shoulders of a human patient, it will be appreciated that the systems and methods herein can be used to assess various other anatomical alignments, distances, etc., in human, animal, or non-living subjects. The systems and methods disclosed herein can be used in minimally-invasive surgery and/or open surgery.

The systems disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A system for assessing anatomical alignment during a surgery, comprising:
   a range finder transceiver and a first attachment element for attaching the range finder transceiver to a first location of a patient;
   a left range finder target and a left attachment element for attaching the left range finder target to a left anatomy of the patient with respect to a sagittal plane of the patient, the left range finder target and the range finder transceiver together defining a left range finder;
   a right range finder target and a right attachment element for attaching the right range finder target to a right anatomy of the patient with respect to the sagittal plane of the patient, the right range finder target and the range finder transceiver together defining a right range finder; and
   a controller configured to:
      measure a first time of flight of a first signal between the range finder transceiver and left range finder target,
      measure a second time of flight of a second signal between the range finder transceiver and right range finder target; and
      compare the first and second times of flight to determine an anatomical alignment of the left and right shoulders or hips of the patient, and
      display an indication of the anatomical alignment of the left and right shoulders or hips of the patient on an electronic display.

2. The system of claim 1, wherein the range finder transceiver comprises a left transceiver configured to be aimed towards the left range finder target and a right transceiver aimed towards the right range finder target.

3. The system of claim 1, wherein the left and right anatomies are the patient's left and right shoulders and wherein the anatomical alignment of the left and right shoulders or hips of the patient comprises a shoulder balance of the patient.

4. The system of claim 1, wherein the left and right anatomies are the patient's left and right hips and wherein the anatomical alignment of the left and right shoulders or hips of the patient comprises a hip balance of the patient.

5. The system of claim 1, wherein the indication is a difference between first and second distances represented by the first and second times of flight on the electronic display.

6. The system of claim 1, wherein the first location comprises a vertebra of the patient.

7. The system of claim 1, wherein the first location comprises a location along the patient's sagittal plane.

8. The system of claim 1, wherein the controller is configured to determine the anatomical alignment of the left and right shoulders or hips of the patient when the sagittal plane of the patient aligns with the patient's central sacral vertical line (CSVL).

9. The system of claim 1, wherein each attachment element comprises at least one of a bone pin and a bone anchor.

10. The system of claim 1, further comprising an alignment guide for aligning at least one of the range finder transceiver, left range finder target and right range finder target with respect to the patient.

11. The system of claim 1,
wherein the left range finder is configured to send the first signal from the range finder transceiver, the first signal then being reflected off the left range finder target and received by the range finder transceiver, and
wherein the right range finder is configured to send the second signal from the range finder transceiver, the second signal then being reflected off the right range finder target and received by the range finder transceiver.

* * * * *